United States Patent [19]

Nelson

[11] Patent Number: 4,543,249

[45] Date of Patent: Sep. 24, 1985

[54] HAIR SPRAY COMPOSITIONS CONTAINING METHYLMETHACRYLATE-METHACRYLIC ACID COPOLYMERS

[75] Inventor: Elliot Nelson, Dobbs Ferry, N.Y.

[73] Assignee: American Cyanamid Co., Stamford, Conn.

[21] Appl. No.: 424,699

[22] Filed: Sep. 27, 1982

Related U.S. Application Data

[63] Continuation of Ser. No. 134,364, Mar. 27, 1980, abandoned, and a continuation-in-part of Ser. No. 9,882, Feb. 6, 1979, abandoned.

[51] Int. Cl.$^4$ .......................... A61K 7/06; A61K 7/11
[52] U.S. Cl. .............................. 424/70; 424/DIG. 1; 424/47; 424/81
[58] Field of Search ............... 424/47, 70, 81, DIG. 1

[56] References Cited

U.S. PATENT DOCUMENTS

| 3,927,199 | 12/1975 | Micchelli et al. | 424/81 |
| 3,934,595 | 1/1976 | Madrange | 424/81 |
| 3,981,987 | 9/1976 | Linke et al. | 424/81 |
| 4,030,512 | 6/1977 | Papantoniou | 424/81 |
| 4,196,190 | 4/1980 | Gehman et al. | 424/81 |

Primary Examiner—Dale R. Ore
Attorney, Agent, or Firm—Charles J. Fickey

[57] ABSTRACT

Hair spray compositions, particularly non-aerosol compositions containing partially to fully neutralized copolymers of 70 to 90 percent methylmethacrylate and 10 to 30 percent methacrylic acid dissolved in aqueous alcohol containing up to 35 percent water.

6 Claims, No Drawings

HAIR SPRAY COMPOSITIONS CONTAINING METHYLMETHACRYLATE-METHACRYLIC ACID COPOLYMERS

CROSS REFERENCE TO RELATED APPLICATIONS

This is a continuation of application Ser. No. 134,364 filed Mar. 27, 1980 now abandoned, and a continuation-in-part of a previous application Ser. No. 9,882, filed Feb. 6, 1979, now abandoned.

The present invention relates generally to hair spray compositions and, in particular, to non-aerosol compositions containing partially to fully neutralized copolymers of 70 to 90 percent methyl methacrylate and 10 to 30 percent methacrylic acid dissolved in aqueous alcohol containing up to 35 percent water.

Hair spray compositions ideally should permit retention of the initial shape of curls over a prolonged period of time in any environment. They should permit curl retention throughout combing and brushing without flaking or powdering and the film produced on the hair by the polymer should be clear and transparent, should give the hair a pleasing feel to the hand, and should not be tacky or feel tacky, especially under humid conditions. Finally, the polymer should be readily and completely removed from the hair on rinsing or shampooing.

The non-aerosol compositions of the present invention provide excellent hair-dressing effects, including improved stiffness, improved curl retention, even in humid environments, and ease of removability by shampooing. Moreover, the compositions do not powder or flake during combing and brushing.

Conventional hair spray compositions have contained shellac, polyvinylpyrrolidone, poly(vinyl methylether), and other polymeric materials as the binding resin for the hair. They have varying degrees of effectiveness and all have defects, such as excessive flaking, softening on exposure to humidity, resulting in loss of curl retention; and some are opaque, giving the hair an unnatural appearance.

Resins have been developed which reduce some of these defects and they include copolymers of vinylacetate and an ester of crotonic acid, acrylic or methacrylic acid, copolymers of vinyl methylether and maleic anhydride, and copolymers of vinylpyrrolidone and an acrylic acid ester. Water soluble films are obtained when the carboxylic acid function in these polymers is neutralized. However, these resins are sensitive to moisture, which negatively affect aesthetics and curl retention. None of the current polymeric resins are completely satisfactory.

It is the object of the present invention to provide non-aerosol hair spray compositions containing aqueous alcoholic solutions of polymeric resins which are water-soluble and removable on shampooing; nonflaking, nontacky; which are transparent, and provide dimensional stability, especially under humid conditions, and provide improved curl retention.

In accordance with the above-stated objects, the present invention provides aqueous alcoholic solutions for non-aerosol, i.e., pump spray, application containing 1 to 10 percent by weight of a copolymer of about 70 to 90 percent methylmethacrylate and 10 to 30 percent methacrylic acid, the carboxyl groups of which are 50 to 100 percent neutralized with a water-soluble base and, optionally, a plasticizer for the copolymer.

Preferably, the hair spray compositions of the invention comprise 1 to 6 weight percent of the copolymer in aqueous alcohol, i.e., 65 to 99 percent ethanol, and 0.05 to 0.5 weight percent of a silicone or fatty acid ester plasticizer for the copolymer.

Especially preferred hair spray compositions of the invention comprise 3 to 6 weight percent of a copolymer containing 80 to 90 percent methylmethacrylate and 10 to 20 percent methacrylic acid, the carboxyl groups of which are 60 to 100 percent neutralized with a water-soluble organic base, dissolved in 93 to 96 percent ethanol and containing a fatty acid plasticizer for the copolymer.

Aerosol hair spray compositions containing copolymers of methylmethacrylate and methacrylic acid are disclosed in the prior art literature. For example, British Patent 1,410,012 discloses aerosol hair spray compositions containing un-neutralized copolymers or terpolymers of methylmethacrylate and methacrylic acid dissolved in a mixture of ethanol and methylene chloride and containing a fluorocarbon propellant system. These copolymers are not useful in the non-aerosol system of the present invention since the polymers are not soluble in aqueous alcohol.

Aerosol hair spray compositions are also described by Kubot et al., U.S. Pat. No. 3,577,517, whereby neutralized polymers containing 5 to 40 weight percent of a long chain ($C_8$ to $C_{18}$) alkyl ester of methacrylic acid are dissolved in anhydrous ethanol and dispensed using a mixture of a hydrocarbon and fluorocarbon propellant. Polymers containing less than 5 weight percent of the long-chain methacrylate ester are said to cause flaking on the hair. Moreover, polymers containing these long-chain esters are insufficiently water-soluble for use in the non-aerosol aqueous alcohol systems of the present invention.

The copolymers of the present invention are readily prepared by conventional polymerization methods by refluxing a solution of the monomers in a water-soluble organic solvent, preferably alcohols, in the presence of an initiator, for example, benzoyl peroxide.

The copolymers are especially suitable for nonaerosol (pump spray) applications, although aerosol formulations may also be utilized.

Copolymers prepared by the co-polymerization of 70 to 90 weight percent methylmethacrylate and 10 to 30 weight percent methacrylic acid are found to provide improved stiffness when applied to the hair, without significantly detracting from the desirable hand feel obtained with resins of lower stiffness. When the copolymers are partially to fully neutralized, they are not tacky and are relatively insensitive to humidity. Moreover, the film on the hair is clear and transparent and does not flake on combing or brushing.

The copolymers are at least about 50% neutralized with a water-soluble base to provide water-solubility and shampoo removability, and preferably, about 60 to 100% neutralized. Examples of suitable water-soluble bases include ammonium hydroxide, sodium hydroxide, potassium hydroxide; mono-, di-, and tripropanolamine, aminomethylpropanol, aminomethylpropanediol, or mixtures thereof. Water-soluble organic bases are preferred and aminomethylpropanol is especially preferred.

Improved results are often achieved, especially if the copolymer contains 90 percent methylmethacrylate, if a plasticizer for the polymer is added to the composition. When used, about 0.05 to 0.5 percent by weight, based on the weight of the copolymer, of either an ester or silicone plasticizer is added. Suitable ester plasticizers include isocetyl stearate, diisopropyladipate, isohexyl laurate, isohexylpalmitate, and isocetyl stearate. Isocetyl stearate is preferred. Suitable silicones include dimethicone copolyol (Silicone Fluid SF-1066, General Electric Co.) which is the reaction product of dimethyl siloxane and ethylene oxide, propylene oxide and/or glycols. Some degree of plasticization is achieved by the water present in the compositions of the invention.

The invention is illustrated by the following examples.

EXAMPLE 1

The following pump spray formulation was prepared using a copolymer of 80% methylmethacrylate (MMA) and 20% methacrylic acid (MAA).

| Composition | % by Weight |
| --- | --- |
| MMA/MAA Copolymer | 4.0 |
| 95% Ethanol | 94.9 |
| Aminomethylpropanol | 0.8 |
| Dow Corning Surfactant 190* | 0.1 |
| Fragrance | 0.2 |
| | 100.0 |

*Silicone glycol copolymer

When the composition was sprayed on clean, virgin tresses, the resin dried to a clear, transparent film, which was not tacky and which did not flake on combing.

EXAMPLE 2

The copolymer of Example 1 was formulated in an aerosol formulation following the procedure of Example 1 of British Patent 1,410,012, as follows:

| Composition | % by Weight |
| --- | --- |
| MMA/MAA Copolymer | 2.25 |
| Ethanol (absolute) | 30.02 |
| Methylene chloride | 7.5 |
| Fragrance | 0.23 |
| Propellant 11/12 (60:40) | 60.0 |
| | 100.00 |

When sprayed on clean, virgin tresses, the resin dried on the hair with a highly visible, heavy white film.

EXAMPLE 3

The following pump spray formulations provide excellent hair-holding characteristics and curl retention, were non-tacky, and gave clear, transparent films.

| Formulation A | |
| --- | --- |
| Composition | % by Weight |
| MMA/MAA Copolymer (80:20) | 5.0 |
| Ethanol (absolute) | 64.0 |
| Water | 30.0 |
| Aminomethylpropanol | 0.5 |
| Dow Corning Surfactant 190 | 0.25 |
| Fragrance | 0.25 |
| | 100.00 |

| Formulation B | |
| --- | --- |
| Composition | % by Weight |
| MMA/MAA Copolymer (70:30) | 5.0 |
| Absolute ethanol | 70.0 |
| Water | 24.0 |
| Triethanolamine (90%) | 0.4 |
| Isocetyl stearate | 0.4 |
| Fragrance | 0.2 |
| | 100.0 |

EXAMPLE 4

A copolymer of 90% methylmethacrylate and 10% methacrylic acid (A) and 80% methylmethacrylate and 20% methacrylic acid (B) and methylvinylether and maleic acid (C) were separately dissolved in 95% ethanol to give a 5.4% solution. Both polymers were neutralized with 1-amino-2-methylpropanol. Films were cast on plate glass and Sward Hardness was measured versus relative humidity for each of three films (A), (B), and (C) at both 40% and 80% relative humidity.

| | Sward Hardness | |
| --- | --- | --- |
| | 40% R.H. | 80% R.H. |
| Polymer A | 18.4 | 17.4 |
| Polymer B | 12.5 | 15.0 |
| Polymer C | 23 | 11.4 |

The data show that Polymers A and B, although initially softer than the Polymer C, remained hard in the presence of high humidity whereas Polymer C got considerably softer. Polymer C is a resin used in commercially available hair sprays.

EXAMPLE 5

A copolymer of 60% methylmethacrylate and 40% methacrylic acid, incorporated into a pump spray formulation similar to Example 1, when applied to clean, virgin tresses, gives a clear, transparent film and possess sufficient stiffness for hair-holding ability.

The use of methyl methacrylate/methacrylic acid copolymers of the present invention allows the use of water and alcohol (ethanol) ratios of up to 99% water. Current commercial resins such as neutralized methylvinyl ether-maleic anhydride copolymer esters allow only water compatibility with alcohol up to 50% water, after which the resin comes out of solution. This greater water compatibility of methyl methacrylate/methacrylic acid neutralized resins allows for less flammability in both pump and aersol applications. Moreover the inclusion of water in the ethanol solvent causes methvinyl ether-maleic anhydride neutralized resins to remain appreciably more sticky than methyl methacrylate/methacrylic acid resins over a time-to-dry cycle.

I claim:

1. A non-aerosol hair spray composition consisting essentially of from about 1 to 10 percent by weight of a copolymer of 70 to 90 percent weight percent methylmethacrylate and 10 to 30 weight percent methacrylic acid, the carboxyl groups of which are 50 to 100 percent neutralized with a water-soluble base, dissolved in 65 to 99 percent aqueous ethanol.

2. A non-aerosol composition according to claim 1 additionally consisting essentially of 0.05 to 0.5 percent by weight, based on the copolymer, of a silicone or fatty acid ester plasticizer.

3. A non-aerosol composition according to claim 1 having 3 to 6 percent by weight of said copolymer, the carboxyl groups of which are 60 to 100 percent neutralized with a water-soluble base, dissolved in 93 to 96 percent aqueous ethanol.

4. A non-aerosol composition according to claim 1 containing a copolymer of 80 to 90 percent by weight methylmethacrylate and 10 to 20 percent by weight methacrylic acid, the carboxyl groups of which are neutralized with a water-soluble organic base.

5. A composition according to claim 1 wherein said base is a water soluble organic base.

6. A composition according to claim 1 wherein said organic base is an organic amine.

* * * * *